(12) United States Patent
Link

(10) Patent No.: US 9,504,580 B2
(45) Date of Patent: Nov. 29, 2016

(54) PLUG-ON MODULE FOR A LONG SHAFT PROSTHESIS

(71) Applicant: WALDEMAR LINK GmbH & Co. KG, Hamburg (DE)

(72) Inventor: Helmut D. Link, Hamburg (DE)

(73) Assignee: WALDEMAR LINK GMBH & CO. KG, Hamburg (DE)

( * ) Notice: Subject to any disclaimer, the term of this patent is extended or adjusted under 35 U.S.C. 154(b) by 0 days.

(21) Appl. No.: 14/417,517

(22) PCT Filed: Jul. 17, 2013

(86) PCT No.: PCT/EP2013/065099
§ 371 (c)(1),
(2) Date: Jan. 26, 2015

(87) PCT Pub. No.: WO2014/016182
PCT Pub. Date: Jan. 30, 2014

(65) Prior Publication Data
US 2015/0190233 A1 Jul. 9, 2015

(30) Foreign Application Priority Data

Jul. 26, 2012 (EP) .................................... 12178008

(51) Int. Cl.
*A61F 2/36* (2006.01)
*A61F 2/30* (2006.01)
(Continued)

(52) U.S. Cl.
CPC .............. *A61F 2/3609* (2013.01); *A61F 2/367* (2013.01); *A61B 17/72* (2013.01); *A61F 2/38* (2013.01);
(Continued)

(58) Field of Classification Search
CPC ........... A61F 2002/30904; A61F 2002/30919; A61F 2/32; A61F 2/3662; A61F 2/3672; A61F 2/3859; A61F 2/389; A61F 2/40; A61F 2/4059; A61F 2/3609

USPC ........... 623/22.4, 22.42, 23.42, 23.15, 23.21, 623/23.23, 19.11–19.14, 22.46, 23.44
See application file for complete search history.

(56) References Cited

U.S. PATENT DOCUMENTS 3,067,740 A * 12/1962 Haboush .................... A61F 2/32
606/328
4,676,797 A * 6/1987 Anapliotis ................ A61F 2/36
623/23.45

(Continued)

FOREIGN PATENT DOCUMENTS

| EP | 1358860 | 11/2003 |
|---|---|---|
| FR | 2788429 | 7/2000 |
| WO | WO-2008/048195 | 4/2008 |

OTHER PUBLICATIONS

International Search Report and Written Opinion mailed Sep. 20, 2013, directed towards International Application No. PCT/EP2013/065099, 10 pages.

(Continued)

*Primary Examiner* — Alvin Stewart
(74) *Attorney, Agent, or Firm* — Morrison & Foerster LLP

(57) ABSTRACT

A plug-on module for pushing onto a free end of a shaft formed for implantation in a long bone, comprising a holding body with an axial bore for the shaft at its lower end and a joint head as a part of a joint endoprosthesis, wherein the joint head is offset downwards in the axial direction from the upper end of the holding body sufficiently far and in such a way that the shaft protrudes upwards beyond the joint head. With such a quasi-offset arrangement the range of usage for the plug-in module is extended to cases in which previously a shorter through-going shaft would have been required and therefore a troublesome adjustment operation to exchange the through-going shaft would have to have been carried out.

16 Claims, 2 Drawing Sheets

(51) Int. Cl.
*A61F 2/38* (2006.01)
*A61B 17/72* (2006.01)

(52) U.S. Cl.
CPC .............. *A61F 2002/3069* (2013.01); *A61F 2002/30331* (2013.01); *A61F 2002/30367* (2013.01); *A61F 2002/30494* (2013.01); *A61F 2002/30507* (2013.01); *A61F 2002/30604* (2013.01); *A61F 2002/30616* (2013.01); *A61F 2002/30795* (2013.01); *A61F 2002/3611* (2013.01); *A61F 2002/3631* (2013.01); *A61F 2250/006* (2013.01)

(56) References Cited

U.S. PATENT DOCUMENTS

| | | | | | |
|---|---|---|---|---|---|
| 4,878,917 | A * | 11/1989 | Kranz | .............. | A61F 2/4637 623/23.45 |
| 5,370,706 | A * | 12/1994 | Bolesky | .............. | A61F 2/36 623/23.44 |
| 5,653,765 | A * | 8/1997 | McTighe | .............. | A61F 2/36 623/18.11 |
| 5,702,480 | A * | 12/1997 | Kropf | .............. | A61F 2/36 623/23.15 |
| 5,725,592 | A * | 3/1998 | White | .............. | A61F 2/36 623/23.35 |
| 5,876,459 | A * | 3/1999 | Powell | .............. | A61F 2/3609 623/23.15 |
| 5,961,555 | A * | 10/1999 | Huebner | .............. | A61F 2/40 623/19.11 |
| 6,099,569 | A * | 8/2000 | Keller | .............. | A61F 2/30721 623/20.15 |
| 6,102,956 | A * | 8/2000 | Kranz | .............. | A61F 2/3662 623/23.15 |
| 6,264,699 | B1 * | 7/2001 | Noiles | .............. | A61F 2/30734 623/20.15 |
| 6,306,174 | B1 * | 10/2001 | Gie | .............. | A61F 2/3609 623/22.42 |
| 6,319,286 | B1 * | 11/2001 | Fernandez | .............. | A61F 2/30734 623/16.11 |
| 6,355,068 | B1 * | 3/2002 | Doubler | .............. | A61F 2/36 623/22.42 |
| 6,443,992 | B2 * | 9/2002 | Lubinus | .............. | A61B 17/164 623/22.11 |
| 6,500,207 | B1 * | 12/2002 | Keller | .............. | A61F 2/384 623/20.15 |
| 6,824,566 | B2 * | 11/2004 | Kana | .............. | A61F 2/3859 623/20.15 |
| 6,843,806 | B2 * | 1/2005 | Hayes, Jr. | .............. | A61F 2/30734 623/23.22 |
| 6,866,683 | B2 * | 3/2005 | Gerbec | .............. | A61F 2/30734 623/18.11 |
| 6,875,239 | B2 * | 4/2005 | Gerbec | .............. | A61F 2/30734 623/23.15 |
| 7,175,664 | B1 * | 2/2007 | Lakin | .............. | A61F 2/36 623/19.14 |
| 7,235,106 | B2 * | 6/2007 | Daniels | .............. | A61F 2/36 623/22.25 |
| 7,255,716 | B2 * | 8/2007 | Pubols | .............. | A61B 17/921 606/99 |
| 7,794,503 | B2 * | 9/2010 | Daniels | .............. | A61F 2/36 623/22.11 |
| 7,867,282 | B2 * | 1/2011 | Heck | .............. | A61F 2/28 606/62 |
| 7,998,218 | B1 * | 8/2011 | Brown | .............. | A61B 17/72 623/20.14 |
| 8,623,093 | B2 * | 1/2014 | Dickerson | .............. | A61F 2/3607 623/19.11 |
| 9,005,305 | B2 * | 4/2015 | Meyers | .............. | A61F 2/3607 623/22.4 |
| 9,161,840 | B2 * | 10/2015 | Hayes, Jr. | .............. | A61F 2/30734 |
| 2002/0004685 | A1 * | 1/2002 | White | .............. | A61F 2/30734 623/23.15 |
| 2002/0040244 | A1 * | 4/2002 | Despres, III | .............. | A61F 2/30734 623/22.15 |
| 2002/0042655 | A1 * | 4/2002 | Hayes, Jr. | .............. | A61F 2/30734 623/23.22 |
| 2003/0050704 | A1 * | 3/2003 | Keynan | .............. | A61B 17/72 623/22.12 |
| 2003/0074078 | A1 * | 4/2003 | Doubler | .............. | A61F 2/36 623/22.42 |
| 2003/0149487 | A1 * | 8/2003 | Doubler | .............. | A61B 17/8605 623/23.44 |
| 2003/0204267 | A1 * | 10/2003 | Hazebrouck | .............. | A61F 2/28 623/23.39 |
| 2003/0204268 | A1 * | 10/2003 | Gerbec | .............. | A61F 2/389 623/23.44 |
| 2003/0204269 | A1 * | 10/2003 | Gerbec | .............. | A61F 2/30734 623/23.47 |
| 2004/0019386 | A1 * | 1/2004 | Ferree | .............. | A61B 17/164 623/23.23 |
| 2004/0054419 | A1 * | 3/2004 | Serra | .............. | A61F 2/4684 623/22.42 |
| 2004/0122525 | A1 * | 6/2004 | Daniels | .............. | A61F 2/36 623/22.42 |
| 2004/0243248 | A1 * | 12/2004 | Despres, III | .............. | A61F 2/30734 623/22.42 |
| 2004/0254646 | A1 | 12/2004 | Stone et al. | | |
| 2005/0004679 | A1 * | 1/2005 | Sederholm | .............. | A61F 2/30734 623/22.42 |
| 2005/0283254 | A1 * | 12/2005 | Hayes, Jr. | .............. | A61F 2/30734 623/22.42 |
| 2006/0041317 | A1 * | 2/2006 | Hazebrouck | .............. | A61F 2/28 623/23.39 |
| 2006/0052877 | A9 * | 3/2006 | Doubler | .............. | A61F 2/36 623/22.42 |
| 2008/0133024 | A1 * | 6/2008 | Meswania | .............. | A61F 2/30734 623/22.42 |
| 2009/0076620 | A1 * | 3/2009 | Khalili | .............. | A61F 2/30721 623/22.42 |
| 2012/0165950 | A1 * | 6/2012 | Baumgart | .............. | A61F 2/3607 623/22.4 |
| 2012/0226361 | A1 * | 9/2012 | Podolsky | .............. | A61B 17/164 623/22.15 |
| 2013/0018482 | A1 * | 1/2013 | Meridew | .............. | A61F 2/30724 623/23.46 |
| 2014/0172115 | A1 * | 6/2014 | Porter | .............. | A61F 2/30739 623/23.15 |
| 2015/0190233 | A1 * | 7/2015 | Link | .............. | A61F 2/367 623/23.42 |
| 2015/0320562 | A1 * | 11/2015 | Porter | .............. | A61F 2/30739 623/22.41 |

OTHER PUBLICATIONS

International Preliminary Report on Patentability issued Jan. 27, 2015, directed towards International Application No. PCT/EP2013/065099, 8 pages.

* cited by examiner

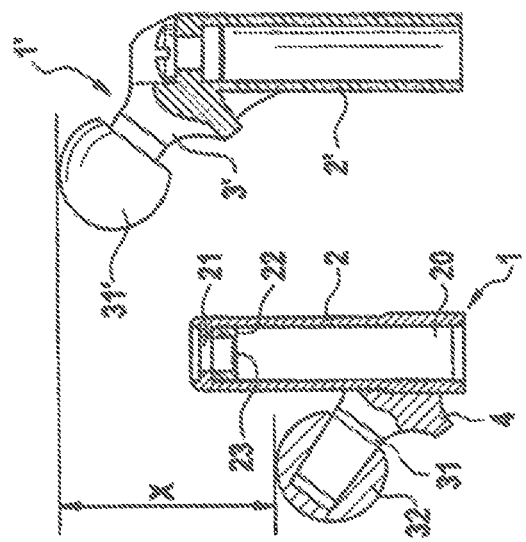
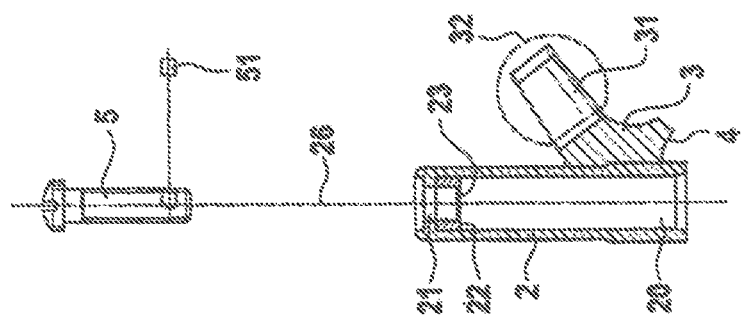
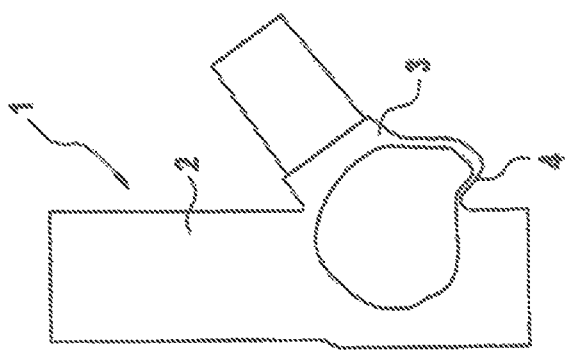

PLUG-ON MODULE FOR A LONG SHAFT PROSTHESIS

REFERENCES TO RELATED APPLICATIONS

This application is a national stage application under USC 371 of International Application No. PCT/EP2013/065099, filed Jul. 17, 2013, which claims priority to European Patent Application No. 12 178 008.4, filed on Jul. 26, 2012.

FIELD OF THE INVENTION

The invention relates to a plug-on module for pushing onto a free end of a shaft to be implanted in a long bone, comprising a holding body, with an axial bore at its lower end for the shaft, and a head element for a joint head as a part of a joint endoprosthesis.

BACKGROUND OF THE INVENTION

Diseases of the long bones, particularly in the extremities, often necessitate the implantation of a long-shafted endoprosthesis, which serves to strengthen the bone and which in many cases also serves at the same time for anchoring a joint element of a joint endoprosthesis, for example a knee prosthesis. Generally, the shaft is inserted into the bone, for example a femur, from the side where the pathological defect is situated. In the case of a knee-joint endoprosthesis, this means that the shaft is usually inserted from the knee end (distal end) of the femur. However, there are also special pathological cases in which the shaft is inserted from the opposite end (i.e., in the case of the knee-joint endoprosthesis, from the proximal end of the femur) and then pushed through the medullary cavity of the bone. Shafts of this kind are generally known by the name "through-going shaft".

A case may arise in which there is also a disease located at the other end of the through-going shaft and requiring treatment with a prosthesis. Taking the example of the knee-joint endoprosthesis, this means that a disease occurs in the area of the hip joint and, consequently, the subsequent implantation of a hip-joint endoprosthesis may be indicated. In practice, this often means that the through-going shaft has to be exchanged. This is a difficult operation and often involves further loss of substance from a bone that is in any case already weakened by disease. Particularly difficult cases are ones in which fractures have already occurred in the damaged joint area (for example, in the case of the hip joint, a fracture of the neck of the femur), which may also result in different lengths of the extremities. This is a severe disadvantage to patients.

SUMMARY OF THE INVENTION

An object of the invention is to reduce these disadvantages and to make a prosthesis of the aforementioned type more universally usable.

This can be achieved by the features as broadly disclosed herein. Advantageous developments are disclosed in the detailed embodiments described below.

In a plug-on module for pushing onto a free end of a shaft designed for implantation in a long bone, comprising a holding body, with an axial bore at its lower end for the shaft, and a head element for a joint head as a part of a joint endoprosthesis, provision is made, according to the invention, that the head element is offset downward in the axial direction from the upper end of the holding body sufficiently far and in such a way that the shaft protrudes upward beyond the joint head. The length by which the shaft protrudes upward beyond the joint head is referred to as the offset.

Joint head is understood as one of the components of a prosthetic joint that determines the position of the center of movement. In a ball-and-socket joint (for example a hip prosthesis), it is the center of the joint ball, and, in the case of a two-part design with a base cone arranged on the holding body and with a plug-on head, the base cone determines the position of the center of movement. In a hinged joint (for example a knee prosthesis), it is the site of the rotation axis that determines the position of the center of movement.

Axial direction is understood as the direction in which the shaft is to be inserted into the axial bore. The indications "downward" and "upward" relate to this axial direction.

An aspect of the invention is the idea of arranging the joint head in a downwardly offset position, i.e. toward the shaft. Thus, the joint head is not located, as it usually is, above the holding body at the free end of the shaft, but instead below this in, as it were, a sunken position. This "sunken" arrangement extends the range of use of the plug-on module to those cases in which a shorter through-going shaft would previously have been required and, therefore, a difficult follow-up operation would need to have been carried out in order to exchange the through-going shaft. With the plug-on module according to the invention, this can be avoided by virtue of the "sunken" arrangement of the joint head. The burden on the patient is thus considerably reduced. Furthermore, there is less risk of complications. The invention thus combines the advantages of an operating technique that entails less work, saves bone substance and greatly reduces the burden on the patient.

Preferably, the joint head is additionally offset in a direction transverse to the axial direction. This can involve in particular the joint head being tilted anteriorly or posteriorly. In this way, the prosthesis according to the invention can also be used in cases in which the disease has caused a modification of the anteversion angle.

Preferably, the axial bore for receiving the shaft is designed as a blind hole. This easily permits an exact positioning of the plug-on module in relation to the shaft. Alternatively, the axial bore can also be designed as a stepped through-bore, wherein an abutment shoulder is provided, beyond which the width of the bore is smaller than the width of the shaft. The part beyond the abutment shoulder serves to receive a securing screw, which fixes the shaft on the plug-on module according to the invention.

A radial toothing is advantageously formed at the bottom of the blind hole or in the area of the abutment shoulder. It is expediently designed as a multiple toothing, with an angle gradation of preferably at least 1° and at most 5°. In this way, the plug-on module can be positioned and secured with precision, and also safely as regards its rotation position with respect to the shaft. By virtue of the sunken arrangement of the multiple toothing, there is no danger of irritation of surrounding tissue.

The joint head is preferably designed in two parts, namely with a base cone arranged on the holding body and with a plug-on head. On the one hand, this permits easy assembly, and, on the other hand, it allows the diameter of the head or the position of the head to be varied through the selection of other heads with a different depth of insertion for the base cone. This greatly increases the variability.

In most cases, the joint head is formed rigidly on the holding body. However, it is also possible that the joint head is arranged on the holding body so as to be variable in position, in order thereby to adopt different offsets. It is thus possible, with just one prosthesis, to cover a great many cases involving correspondingly different offsets.

A collar-like projection protruding in the caudal-medial direction is expediently provided on the joint head. It functions as a bearing and has the effect that the force initiated by the prosthesis in particular when the patient is standing or walking can be better transmitted to the femur.

The holding body is expediently designed such that the axial bore forms a long shaft receiver for the shaft. Long shaft is understood here as meaning that the depth of the receiving bore is at least four times the width of the shaft. Thus, even in the case of considerable loads, in particular when the patient is taking part in a sports activity, it is possible to achieve a long-term stable anchoring of the shaft in the holding body.

The invention further relates to a kit comprising several plug-on modules of the type described above, wherein the plug-on modules differ from each other in that the joint heads are offset to different extents. The operating surgeon is thus afforded the possibility of selecting, from a large number of options, the size best suited to the particular circumstances presented by the patient.

BRIEF DESCRIPTION OF THE DRAWINGS

The invention is explained in more detail below on the basis of an illustrative embodiment depicted in the attached drawing, in which:

FIG. 1 shows a view of a plug-on module according to an illustrative embodiment;

FIG. 2 shows a cross-sectional view of the illustrative embodiment depicted in FIG. 1, with a fastening screw;

FIG. 3 shows a view allowing the offset of the plug-on module to be compared against a conventional design.

DETAILED DESCRIPTION OF THE INVENTION

Figure 4:
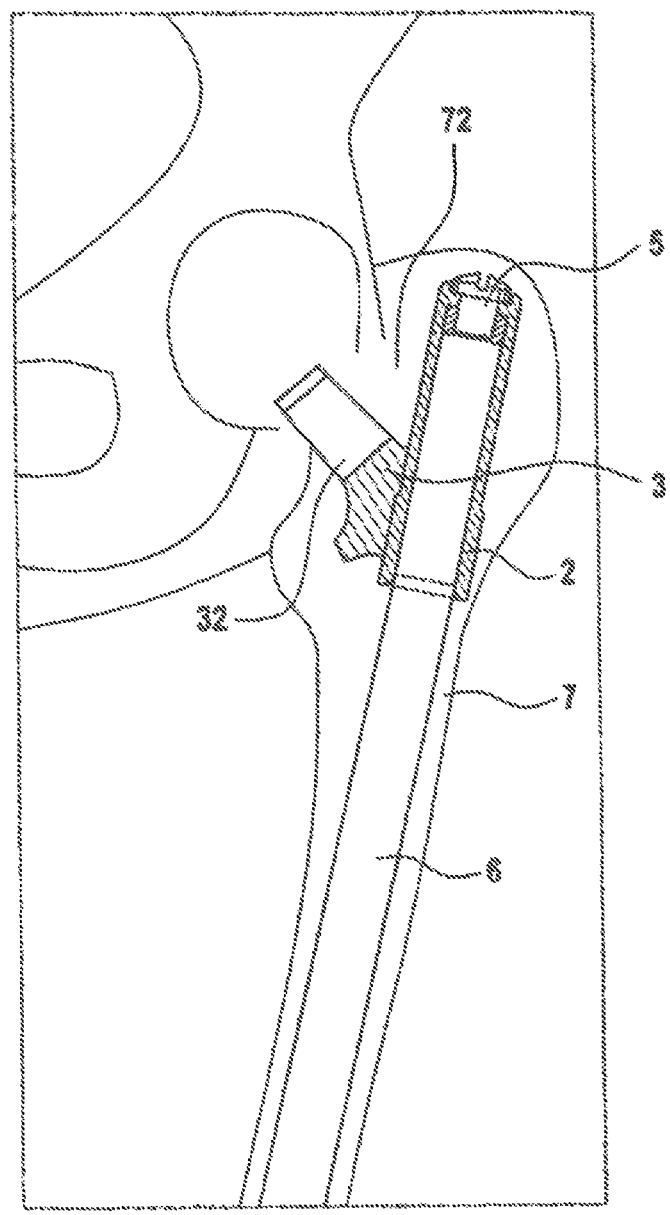
FIG. 4 shows an X-ray image depicting the position of the plug-on module according to the invention in the femur.

A plug-on module, designated in its entirety by reference number 1, comprises a tubular holding body 2 and a joint head 3. The joint head 3 is arranged laterally on the holding body 2, in the lower third, and protrudes obliquely upward.

At its lower end, the holding body 2 has a mouth for a receiving bore 20. The receiving bore 20 is dimensioned such that a free end of a through-going shaft 6 (see FIG. 4) can be received in a manner free of play. The receiving bore 20 is of cylindrical configuration and is oriented in the axial direction 26 of the holding body 2. The receiving bore 20 has a depth that measures five times its diameter. The upper end of the receiving bore 20 is delimited by an abutment shoulder 22, which is provided with a downwardly directed multiple radial toothing 23. The latter cooperates with a corresponding mating toothing on the free end of the through-going shaft 6 and, in the plugged-on state, thus secures the plug-on module 1 against undesired twisting in relation to the through-going shaft 6.

In the upper area of the holding body 2, the receiving bore 20 is continued along the axial direction 26 by a stepped bore 21. The latter serves to receive a securing screw 5, which is inserted from above into the stepped bore 21 and is screwed with its thread into the through-going shaft 6 and thus secures the latter. To prevent undesired loosening of the securing screw 5, a stop element 51 made of plastic is inserted laterally.

The joint head 3 is formed integrally with the holding body 2 and has, in its outer area protruding obliquely upward, an outer cone 31. The latter functions as a receiver for a ball head 32, which is provided with a complementary inner cone and is mounted in a manner free of play for the implantation. A projection 4 protruding obliquely downward is also formed on the joint head 3. It serves as an additional bearing of the holding piece 2 in the area of a resected neck of the femur 7 in which the plug-on module 1 is implanted with the through-going shaft 6.

FIG. 3 shows the axial offset of the joint head 3 in relation to a conventional plug-on module 1'. Whereas the joint head 3' in the conventional plug-on module 1' is arranged at the upper end of the holding body 2' and extends still further above, the joint head 3 in the plug-on module 1 according to the invention is by contrast downwardly offset by an extent "X". The joint head 3 is located below the upper end of the holding body 2, so to speak in a sunken arrangement. In this way, the plug-on module 1 according to the invention can provide remedy in all cases where the use of a conventional plug-on module 1' is no longer possible.

Such a case is shown in FIG. 4. This represents the X-ray image of a hip joint with the upper part of a femur 7, including the neck 72 of the latter. A through-going shaft 6 from an earlier implantation of a knee-joint endoprosthesis is already present in the femur 7. Pathological changes have caused the head of the hip joint to migrate downward and have caused the neck of the femur to break. There is therefore a need for a hip-joint endoprosthesis. On account of the broken neck 72 of the femur, the length of the leg is shortened. If a conventional plug-on module 1' were used, the through-going shaft 6 would have to be exchanged. With the plug-on module 1' according to the invention, the shortening of the leg can be compensated by the joint head being arranged farther down by the offset X. This allows the existing through-going shaft to be retained and thus permits substantial preservation of the bone and of the associated ligament apparatus of the hip joint.

The invention claimed is:

1. A plug-on module for pushing onto a free end of a shaft configured for implantation in a long bone, comprising a holding body, the holding body comprising:
   a bore at a lower end of the holding body for receiving the shaft, wherein the bore comprises a longitudinal axis, and
   a joint head configured to form a joint portion of a joint endoprosthesis, wherein the joint head is offset downward in a direction extending along the longitudinal axis of the bore from an upper end of the holding body such that, when installed, the shaft protrudes upward beyond the joint head.

2. The plug-on module of claim 1, wherein the joint head is additionally offset in a direction extending transversely to the longitudinal axis of the bore.

3. The plug-on module of claim 2, wherein the joint head is tilted anteriorly or posteriorly from a plane of the direction extending along the longitudinal axis of the bore.

4. The plug-on module of claim 1, wherein the bore for receiving the shaft is configured as a blind hole.

5. The plug-on module of claim 4, wherein one or both of a radial toothing and a cone for the connection are arranged at the bottom of the blind hole.

6. The plug-on module of claim 5, wherein the radial toothing is configured as a multiple toothing.

7. The plug-on module of claim 6, wherein the multiple toothing has an angle gradation of at least 1° and at most 5°.

8. The plug-on module of claim 1, wherein the bore is configured as a stepped through-bore.

9. The plug-on module of claim 8, wherein the stepped through-bore comprises an abutment shoulder beyond which the width of the bore is smaller than the width of the shaft.

10. The plug-on module of claim 9, wherein one or both of a radial toothing and a cone for the connection are arranged on the abutment shoulder.

11. The plug-on module of claim 1, wherein the joint head is configured in two parts.

12. The plug-on module of claim 11, wherein the two parts comprise a base cone arranged on the holding body and with a plug-on head.

13. The plug-on module of claim 1, wherein the joint head is arranged on the holding body so as to be variable in its offset position.

14. The plug-on module of claim 1, wherein the bore forms a long shaft receiver for the shaft.

15. A kit comprising multiple plug-on modules for pushing onto a free end of a shaft configured for implantation in a long bone, each plug-on module comprising a holding body, the holding body comprising:
 a bore at a lower end of the holding body for receiving the shaft, wherein the bore comprises a longitudinal axis, and
 a joint head configured to form a joint portion of a joint endoprosthesis, wherein the joint head is offset downward in a direction extending along the longitudinal axis of the bore from an upper end of the holding body such that, when installed, the shaft protrudes upward beyond the joint head,
 wherein at least one joint head of the multiple pug-on modules is offset to a different extent than at least one other joint head of the multiple plug-on modules.

16. The kit of claim 15, wherein each plug-on module is further configured such that the joint head is additionally offset in a direction extending transversely to the longitudinal axis of the bore.

* * * * *